US010117585B2

(12) United States Patent
Kobayashi et al.

(10) Patent No.: US 10,117,585 B2
(45) Date of Patent: Nov. 6, 2018

(54) SENSOR AND BIOLOGICAL SIGNAL MEASURING SYSTEM

(71) Applicant: NIHON KOHDEN CORPORATION, Tokyo (JP)

(72) Inventors: Naoki Kobayashi, Tokyo (JP); Hideaki Hirabara, Tokyo (JP); Katsuyuki Horie, Tokyo (JP); Tsuyoshi Shimizu, Tokyo (JP); Kota Saeki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 108 days.

(21) Appl. No.: 14/852,587

(22) Filed: Sep. 13, 2015

(65) Prior Publication Data

US 2016/0089036 A1   Mar. 31, 2016

(30) Foreign Application Priority Data

Sep. 29, 2014  (JP) .................................. 2014-198149
Sep. 7, 2015   (JP) .................................. 2015-175300

(51) Int. Cl.
*A61B 5/02* (2006.01)
*A61B 5/00* (2006.01)
(Continued)

(52) U.S. Cl.
CPC ........ *A61B 5/02028* (2013.01); *A61B 5/0059* (2013.01); *A61B 5/0261* (2013.01);
(Continued)

(58) Field of Classification Search
CPC .............. A61B 5/02028; A61B 5/0059; A61B 5/02233; A61B 5/0261; A61B 5/6831;
(Continued)

(56) References Cited

U.S. PATENT DOCUMENTS 3,040,737 A * 6/1962 Kompelien ........ A61B 5/02255
356/39
3,906,937 A * 9/1975 Aronson ............ A61B 5/02141
600/493

(Continued)

FOREIGN PATENT DOCUMENTS

EP   2 762 075 A1   8/2014
JP   6-30915 A      2/1994
(Continued)

OTHER PUBLICATIONS

European Search Report for Patent Application No. EP 15 18 5419, dated Feb. 24, 2016.

(Continued)

*Primary Examiner* — Lindsey G Wehrheim
(74) *Attorney, Agent, or Firm* — Pearne & Gordon LLP

(57) ABSTRACT

A biological signal measuring system includes a sensor and a biological signal measuring apparatus configured to calculate a blood refill time of a living tissue of a subject. The sensor includes a pressure applying portion configured to apply pressure on the living tissue, a light emitter configured to emit light toward the living tissue, a light receiver configured to receive reflected light or transmitted light from the living tissue, a first light transmitting member made of a light transmitting material and having one side contacting the light emitter and the other side arranged to contact the subject, a second light transmitting member made of a light transmitting material and having one side contacting the light receiver and the other side arranged to contact the subject, and a light blocking member configured to block light between the light emitter and the light receiver.

16 Claims, 11 Drawing Sheets

(51) Int. Cl.
*A61B 5/022* (2006.01)
*A61B 5/026* (2006.01)
*A61B 5/024* (2006.01)

(52) U.S. Cl.
CPC ........ *A61B 5/02233* (2013.01); *A61B 5/6831* (2013.01); *A61B 5/6832* (2013.01); *A61B 5/0053* (2013.01); *A61B 5/02422* (2013.01); *A61B 5/6814* (2013.01); *A61B 5/6824* (2013.01); *A61B 5/6828* (2013.01); *A61B 2560/0462* (2013.01)

(58) Field of Classification Search
CPC . A61B 5/6832; A61B 5/0053; A61B 5/02422; A61B 5/6814; A61B 5/6824; A61B 5/6828; A61B 2560/0462
See application file for complete search history.

(56) References Cited

U.S. PATENT DOCUMENTS

| | | | |
|---|---|---|---|
| 4,846,189 A * | 7/1989 | Sun | A61B 5/02007 600/480 |
| 5,385,143 A | 1/1995 | Aoyagi | |
| 2007/0282182 A1 | 12/2007 | Messerges et al. | |
| 2009/0105556 A1* | 4/2009 | Fricke | A61B 5/0059 600/301 |
| 2009/0143655 A1* | 6/2009 | Shani | A61B 5/0059 600/323 |
| 2012/0046561 A1 | 2/2012 | Usuda et al. | |
| 2012/0130211 A1 | 5/2012 | Kobayashi et al. | |
| 2014/0213884 A1 | 7/2014 | Hirabara et al. | |
| 2014/0275891 A1 | 9/2014 | Muehlemann et al. | |
| 2014/0276149 A1 | 9/2014 | Takahashi et al. | |

FOREIGN PATENT DOCUMENTS

| | | |
|---|---|---|
| JP | 2012-40088 A | 3/2012 |
| JP | 2012-115640 A | 6/2012 |

OTHER PUBLICATIONS

European Office action issued in Patent Application No. EP 15 185 419 dated Jul. 31, 2018.

* cited by examiner

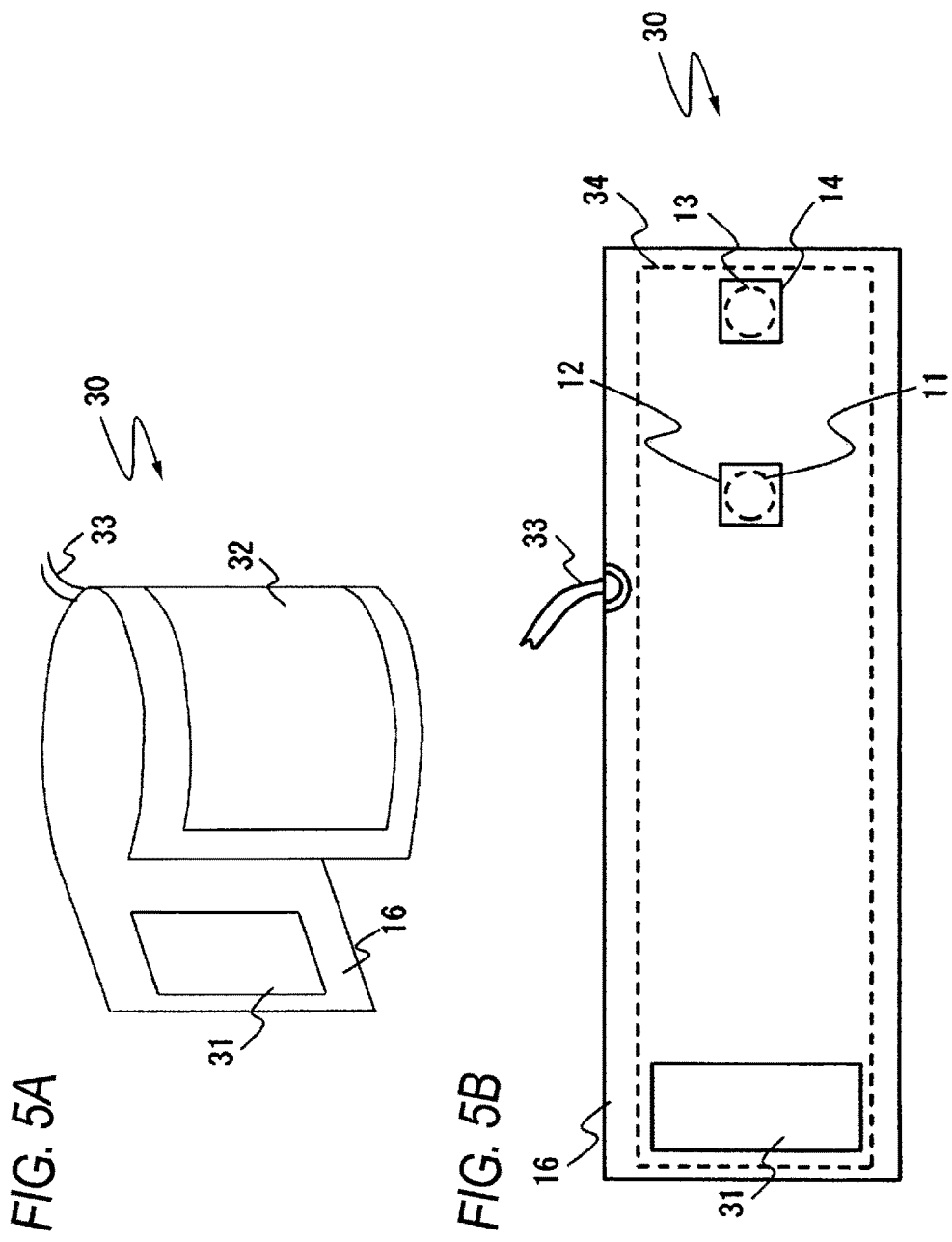

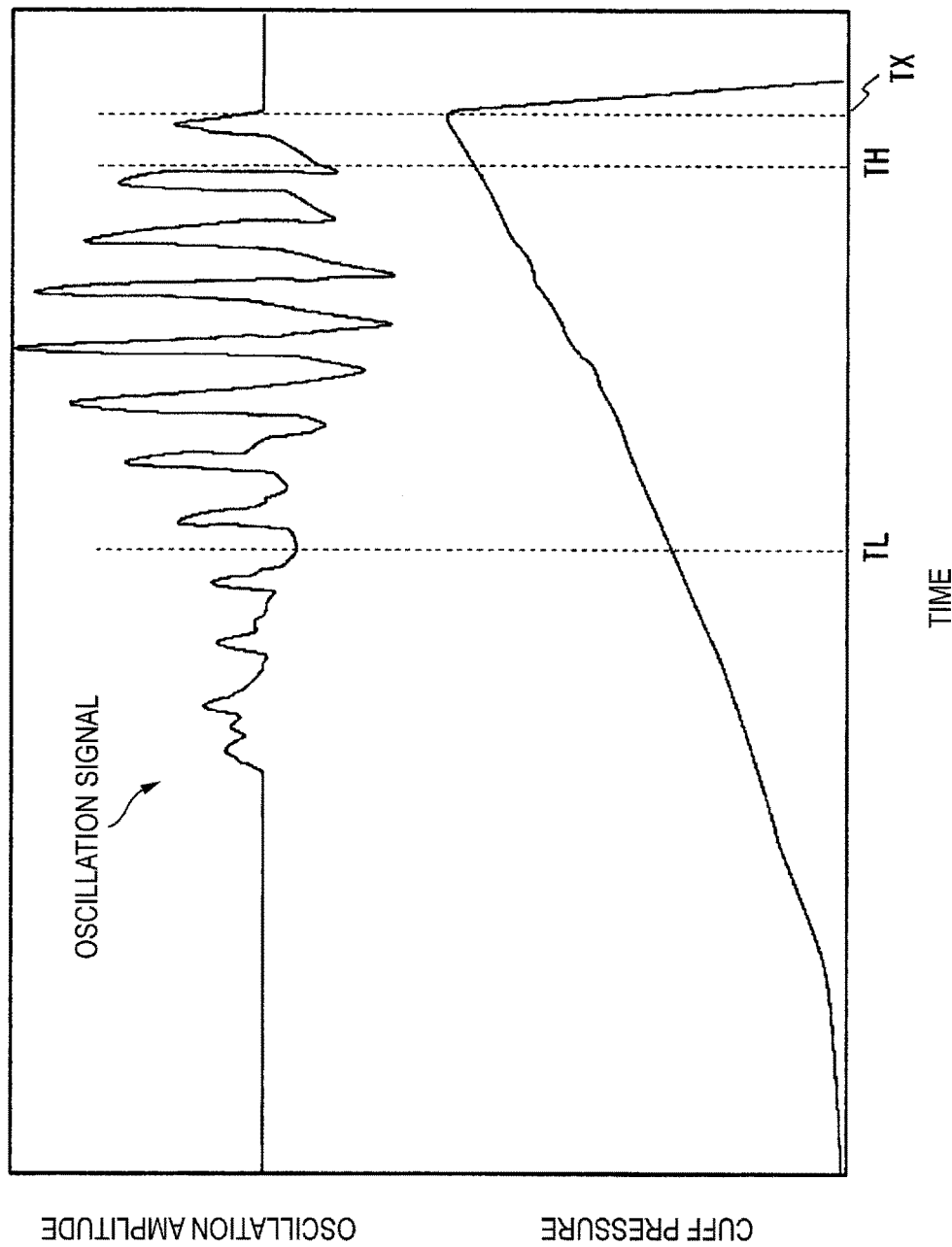

SENSOR AND BIOLOGICAL SIGNAL MEASURING SYSTEM

CROSS-REFERENCE TO RELATED APPLICATION(S)

The present application claims priority from Japanese Patent Application No. 2014-198149 filed on Sep. 29, 2014 and Japanese Patent Application No. 2015-175300 filed on Sep. 7, 2015, the entire content of which is incorporated herein by reference.

BACKGROUND

The presently disclosed subject matter relates to a sensor and a biological signal measuring system.

A blood refill time is one of indexes for observing a tissue perfusion of a subject. The blood refill time is used as a simple index for evaluating whether shock has occurred. The blood refill time is widely used in the field of emergency medicine for the purpose of determining necessity of transfusion, triage (evaluation of priority in a case where many persons are injured or sickened) or the like.

Generally, when measuring a blood refill time, a medical person applies pressure on a living tissue of a subject, such as a finger nail, and after the pressure is released, visually checks the color change of the nail or the skin. When the color returns to an original color within approximately two seconds, it is determined that the subject is in a normal condition. In this technique, however, because the living tissue is manually pressed and the change of the skin color is visually checked, it cannot provide quantitative results and an error easily occurs.

A related art blood refill time measurement uses a pulse oximeter (see, e.g., US2007/0282182A1). More specifically, light of a wavelength which can be absorbed by blood enters living tissue, and the intensity of light which transmits through the living tissue is measured by an optical sensor. In this case, when the living tissue is pressed by using an actuator, blood is evacuated from the living tissue of the pressed portion, and hence the intensity of the transmitted light is increased. When the pressure is released, the living tissue of the portion is filled with blood, and therefore the intensity of the transmitted light is decreased. The blood refill time is identified based on the time elapsed from the release of the pressure until the transmitted light intensity returns to the original level.

In order to perform a reproducible and quantitative measurement of the blood refill time, it is necessary to provide the same condition of applying pressure on living tissue. In the configuration where the living tissue is directly pressed by an actuator, however, it is difficult to always bring the actuator to contact the same portion of the living tissue. When the contacting position changes, the condition of applying pressure also changes, and therefore the reproducibility of measurement results is lowered.

The living tissue may compressed by using an air bag or the like. Depending on the material of the air bag, however, the light entering the living tissue, and the transmitted light (or reflected light) from the living tissue are affected, and the accuracy of measurement results may be lowered.

SUMMARY

Illustrative aspects of the present invention provide a sensor and a biological signal measuring system configured to perform an accurate measurement of blood refill time.

According to an illustrative aspect of the present invention, a sensor is configured to measure a blood refill time of a living tissue of a subject. The sensor includes a pressure applying portion configured to apply pressure on the living tissue of the subject, a light emitter configured to emit light toward the living tissue of the subject, a light receiver configured to receive reflected light or transmitted light from the living tissue of the subject, a first light transmitting member made of a light transmitting material and having one end configured as a contact surface contacting the light emitter and another end forming a contact surface to contact the subject, a second light transmitting member made of a light transmitting material and having one end configured as a contact surface contacting the light receiver and another end forming the contact surface to contact the subject, and a light blocking member configured to block light between the light emitter and the light receiver.

According to another illustrative aspect of the present invention, a biological signal measuring system includes the sensor described above, and a biological signal measuring apparatus configured to calculate the blood refill time of the subject based on an amount of light received by the sensor.

BRIEF DESCRIPTION OF DRAWINGS

FIGS. 5A and 5B are external views of a cuff as an example of the sensor;

FIG. 7 is a chart showing a relationship between an inflation of the cuff and an oscillation signal;

DETAILED DESCRIPTION

Figure 1:
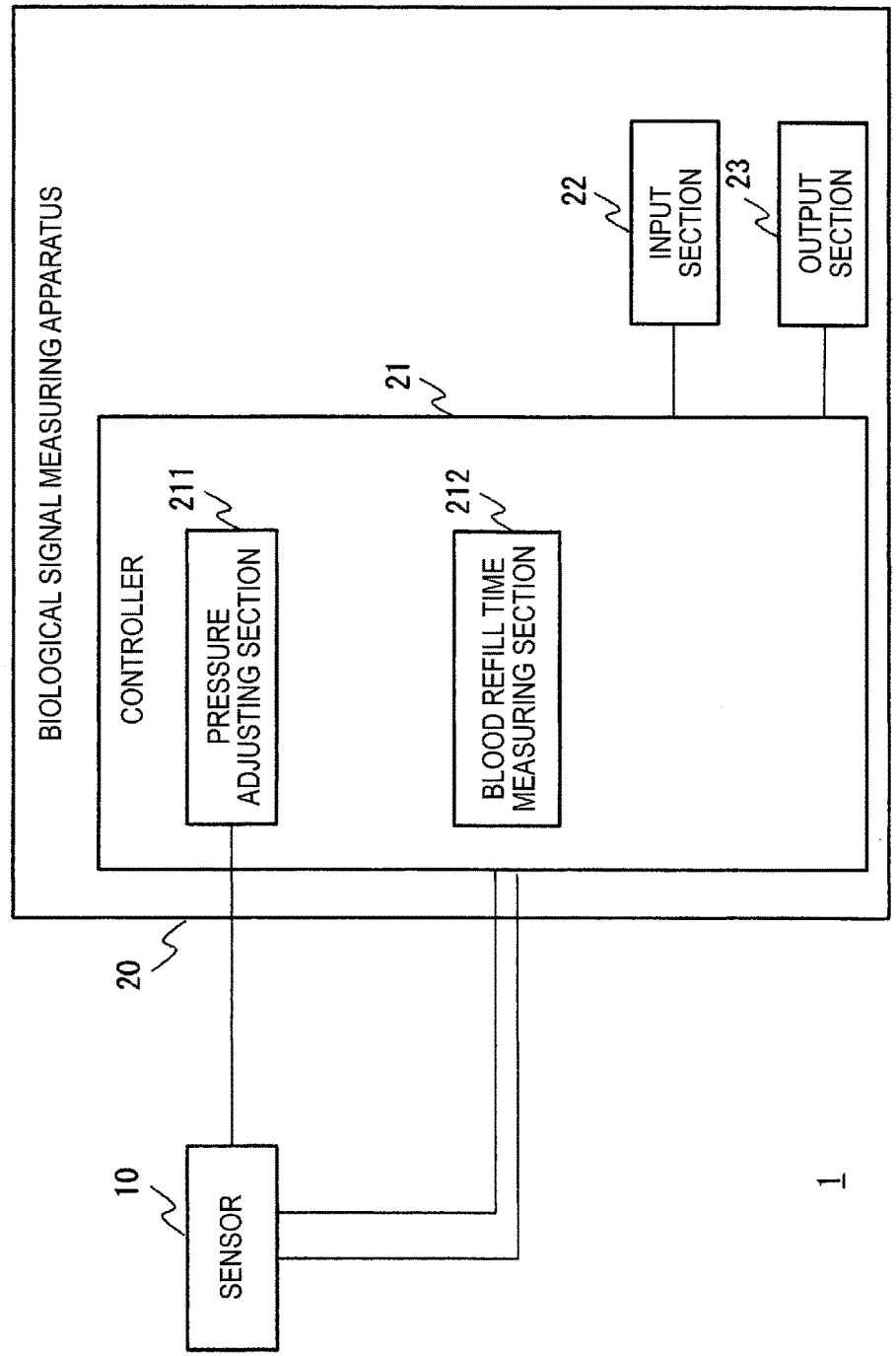
FIG. 1 is a block diagram illustrating a configuration of a biological signal measuring system according to an exemplary embodiment of the present invention.

Hereinafter, exemplary embodiments of the present invention will be described in detail with reference to the drawings. FIG. 1 is a block diagram illustrating a configuration of a biological signal measuring system. The biological signal measuring system 1 includes a sensor 10 and a biological signal measuring apparatus 20.

The sensor 10 is used for measuring a blood refill time of a subject. The sensor 10 is configured to apply pressure on a living tissue (for example, an arm or a forehead) of the subject, emit light toward the living tissue, and receive reflected light or transmitted light from the living tissue. The sensor 10 sends a detection signal indicating the amount of light received from the living tissue to the biological signal measuring apparatus 20. The configuration of the sensor 10 will be described later with reference to FIG. 3.

The biological signal measuring apparatus 20 includes a controller 21, an input section 22, and an output section 23. The controller 21 includes a pressure adjusting section 211 and a blood refill time measuring section 212.

The pressure adjusting section 211 adjusts the strength of pressure applied by the sensor 10 to the living tissue of the subject. Specifically, the pressure adjusting section 211 sends a control signal (hereinafter, a pressure control signal) to the sensor 10 to control the strength of pressure applied to the subject by the sensor 10. Generally, it is considered that the normal blood refill time is two seconds or less. Therefore, the pressure adjusting section 211 reduces the pressure so that the time period from the start of reduction of the pressure to the end of the application of pressure is shorter than two seconds (i.e., the time constant of the pressure reduction is equal to or less than two seconds).

The controller 21 controls the amount of light to be emitted from the sensor 10 and the timing of the light emission by using a control signal. The blood refill time measuring section 212 acquires the amount of light received by the sensor 10 in each of time periods (for example, before the start of the application of pressure, during the application of pressure, and after the end of the application of pressure). Then, the blood refill time measuring section 212 measures the blood refill time in accordance with a change in the amount of received light. The process of measuring the blood refill time will be described in detail with reference to the flowchart of FIG. 2.

Firstly, the controller 21 starts emission and reception of light at a predetermined timing (for example, every 30 minutes) (S11). In this step, the pressure adjusting section 211 performs a control so as not to apply pressure on the living tissue. The blood refill time measuring section 212 measures the amount of received light before an application of pressure on the living tissue, from the sensor 10 (S12). After acquisition of the amount of received light before the application of pressure, the pressure adjusting section 211 starts to apply pressure on the living tissue (S13). The blood refill time measuring section 212 measures the amount of received light in the state of pressure being applied on the living tissue, from the sensor 10 (S14). After the application of pressure is sufficiently performed, the pressure adjusting section 211 releases the pressure on the living tissue (S15).

The blood refill time measuring section 212 computes or calculates the time elapsed from the timing when the pressure on the living tissue is released, until when the amount of received light attenuates to a value that is approximately equal to that before the application of pressure, as the blood refill time (S16). An example of a method of calculating the blood refill time is disclosed in JP2012-115640A.

The blood refill time may be calculated by using a change of the amount of received light after the application of pressure, without using the amount of received light before the application of pressure. That is, the blood refill time measuring section 212 may use any kind of algorithm in so far as the blood refill time can be identified by using a change of the amount of received light after the application of pressure on the living tissue.

Referring again to FIG. 1, the input section 22 is configured by input interfaces such as buttons and knobs disposed on the biological signal measuring apparatus 20, a control circuit for the interfaces, and the like.

The output section 23 outputs the blood refill time which is measured by the controller 21. For example, the output section 23 displays the blood refill time on a liquid crystal display disposed on the housing of the biological signal measuring apparatus 20. The outputting process by the output section 23 includes not only the display on the screen, but also a print output, writing into an electronic file, and the like.

The input section 22 and the output section 23 may be configured such that the display of information and the operation input can be simultaneously performed as in a touch panel.

Figure 3:
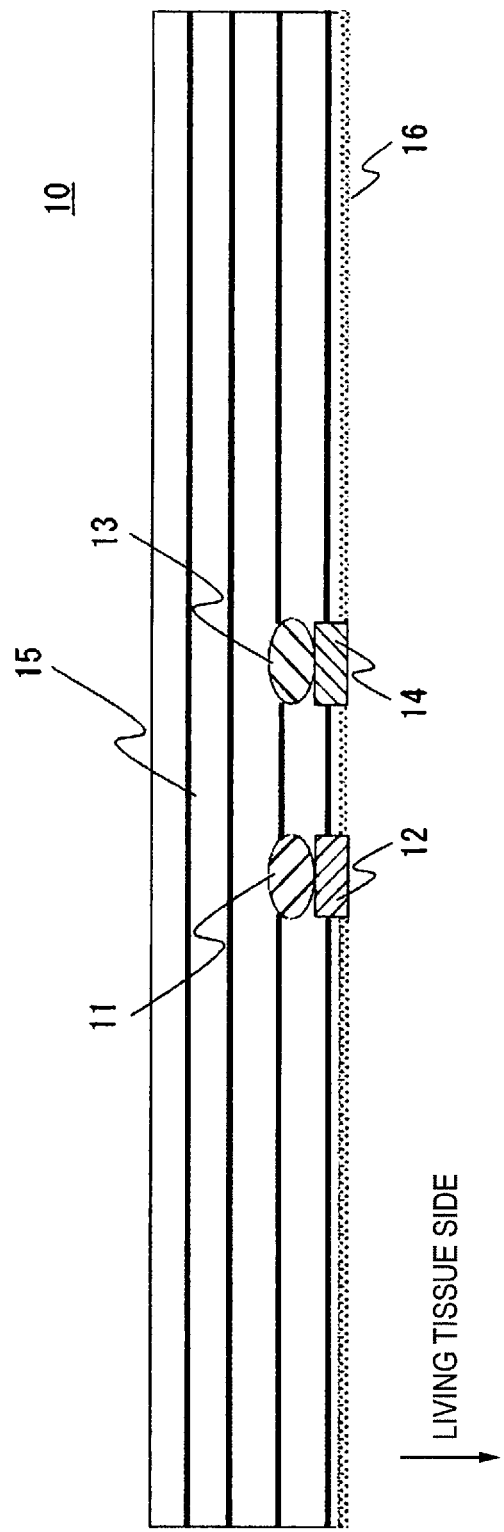
FIG. 3 is a sectional view of a sensor according to an exemplary embodiment of the present invention.

Next, the configuration of the sensor 10 will be described with reference to FIG. 3. FIG. 3 is a sectional view of the sensor 10. The sensor 10 is attached to a head, an arm or the like of the subject. The sensor 10 emits light of a predetermined wavelength toward the living tissue, and receives reflected light or transmitted light from the living tissue. Specific examples of the sensor 10 will be later described.

The sensor 10 includes a light emitter 11, a first light transmitting member 12, a light receiver 13, a second light transmitting member 14, and a light blocking member 15. A contact surface 16 contacts a surface of a living tissue of a subject.

The light emitter 11 emits light of a predetermined wavelength toward the living tissue of the subject (downward in FIG. 3). The light emitted from the light emitter 11 passes through the first light transmitting member 12 and enters the living tissue of the subject. The light emitter 11 has a light emitting device that emits light. The light emitting device is, for example, a laser diode, a light emitting diode (LED) or the like. The light emitter 11 may include a plurality of light emitting devices, and the light emitting devices may respectively emit light of different wavelengths (for example, 660 nm and 940 nm) at timings in accordance with the control by the controller 21.

The first light transmitting member 12 is configured to guide the light emitted from the light emitter 11 toward the living tissue of the subject. That is, the first light transmitting member 12 is arranged such that one side (one end) of the first light transmitting member 12 provides a contact surface contacting the light emitter 11, and the other side (other end) of the first light transmitting member 12 provides a contact surface to contact the subject. The first light transmitting member 12 is made of a material having a high light transmission rate (light transmitting material), such as silicon rubber, elastomer, polyvinyl chloride, polycarbonate, ABS, polyurethane, plant fibers, or nylon. The light transmission rate of the first light transmitting member 12 is preferably about 30% to 100%.

The second light transmitting member 14 is configured to guide reflected light or transmitted light from the living tissue of the subject toward the light receiver 13. That is, the second light transmitting member 14 is arranged such that one side (one end) of the second light transmitting member 14 provides a contact surface contacting the light receiver 13, and the other side (other end) the second light transmitting member 14 provides a contact surface to contact the subject. The second light transmitting member 14 is made of a material having a high light transmission rate (light transmitting material), such as silicon rubber, elastomer, polyvinyl chloride, polycarbonate, ABS, polyurethane, plant fibers, or nylon. The light transmission rate of the second light transmitting member 14 is preferably about 30% to 100%.

The light receiver 13 receives reflected light or transmitted light from the living tissue of the subject. The light receiver 13 sends a light reception signal corresponding to the amount of received light (intensity of the received light), to the biological signal measuring apparatus 20. The light receiver 13 produces the light reception signal by a light receiving device provided therein. An example of the light receiving device is a photodiode.

The light blocking member 15 is disposed between the light emitter 11 and the light receiver 13, and has a low light transmission rate. In other words, the light blocking member 15 has a lower light transmission rate (second light transmission rate) than the light transmission rate (first light transmission rate) of the first light transmitting member 12 and the second light transmitting member 14. The light blocking member 15 is configured to block light so that the light emitted from the light emitter 11 is not directly received by the light receiver 13. The light blocking member 15 is made of, for example, silicon rubber to which pigment is added, elastomer, polyvinyl chloride, polycarbonate, ABS, polyurethane, plant fibers, or neoprene. The light transmission rate of the light blocking member 15 is preferably about 0% to 30%.

In the example of FIG. 3, the light blocking member 15 is configured so as to cover the light emitter 11 and the light receiver 13. However, the present invention is not limited to this. The light blocking member 15 may be configured and arranged in any other ways in so far as it prevents the light from traveling directly to the light receiver 13 from the light emitter 11. For example, the light blocking member 15 may be a wire-like member configured to block the direct light transmission between the light emitter 11 and the light receiver 13.

The light blocking member 15 may also function as a pressure applying portion configured to apply pressure on the living tissue of the subject, as in the later described examples. For example, the light blocking member 15 may be a bag of a cuff or the like. Pressure may be applied to the living tissue of the subject by a detachable belt or the like (pressure applying portion) through the sensor 10, as will be described later with reference to FIG. 10.

Advantages of the configuration described above and shown in FIGS. 1 to 3 will be described. The light emitter 11 emits light toward the living tissue of the subject through the first light transmitting member 12 made of a light transmitting material. That is, the light from the light emitter 11 enters the living tissue of the subject without being attenuated. Therefore, the light emitter 11 can provide sufficient amount of light for measuring the blood refill time to enter the living tissue of the subject.

The light receiver 13 directly receives light (reflected light or transmitted light) from the living tissue of the subject, through the second light transmitting member 14 which is made a light transmitting material. Therefore, the light receiver 13 can perform a light receiving process which is affected by nothing other than the living tissue.

The light blocking member 15 is disposed between the light emitter 11 and the light receiver 13. Therefore, the light receiver 13 can avoid being directly affected by the light emission of the light emitter 11.

These functions ("a sufficient amount of light can enter the living tissue," "light from the living tissue can be directly received," and "the light receiver 13 is not directly affected by the light emission of the light emitter 11") allow the sensor 10 to correctly acquire only a change in the amount of light caused by the living tissue of the subject.

Figure 2:
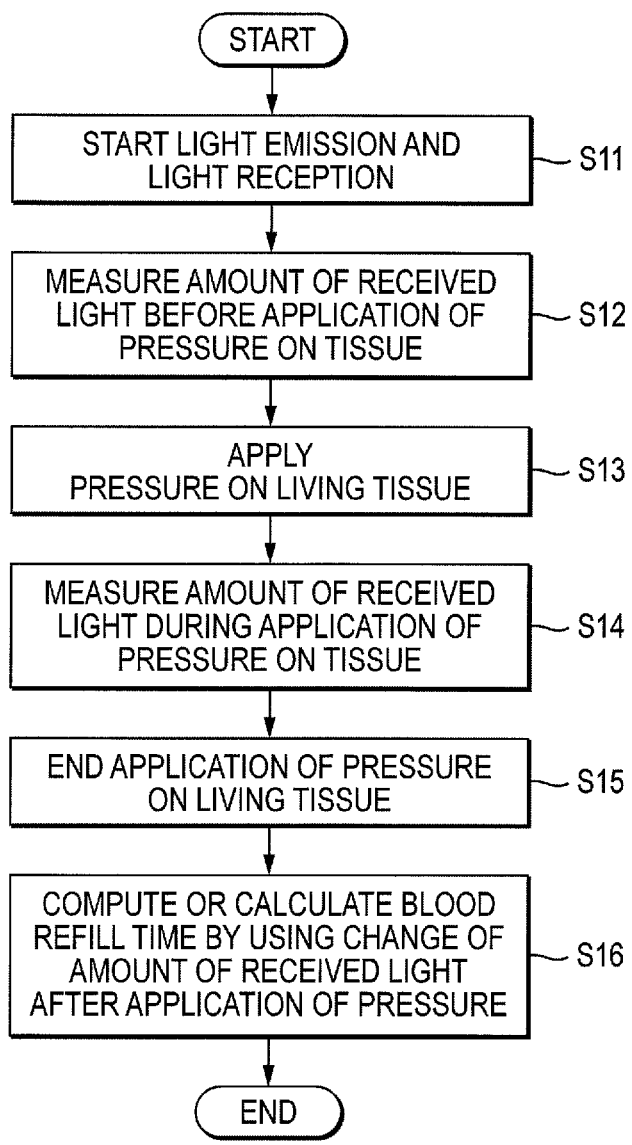
FIG. 2 is a flowchart illustrating steps for measuring blood refill time according to an exemplary embodiment of the present invention.

Hereinafter, specific examples of the above-described configuration (FIGS. 1 to 3) will be described. In the following description, the elements identified by the same names and reference numerals as those of FIGS. 1 to 3 are configured to perform the same functions as those described above unless otherwise described.

Figure 4:
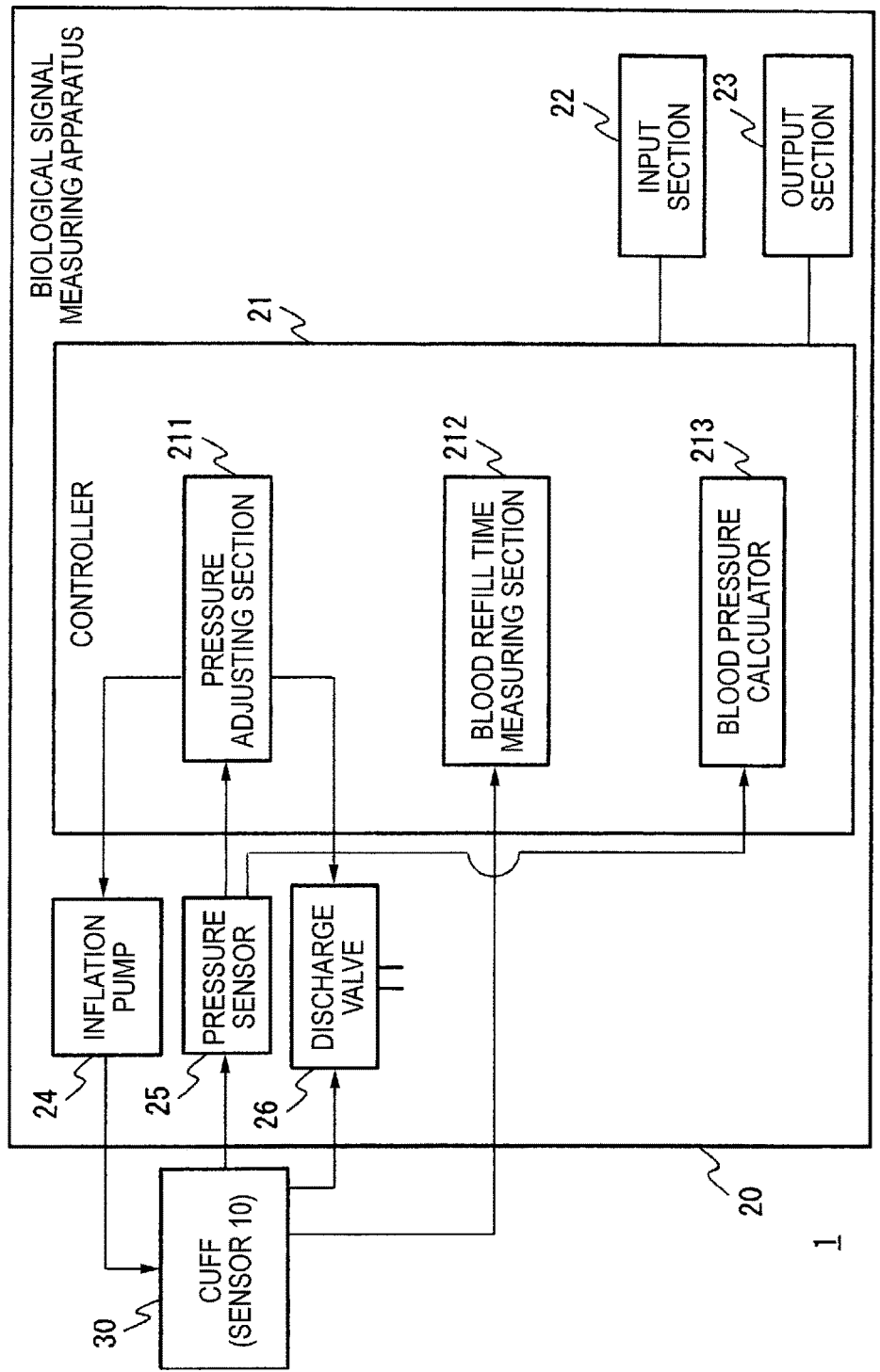
FIG. 4 is a block diagram illustrating a configuration of a biological signal measuring system according to another exemplary embodiment of the present invention.

According to an exemplary embodiment of the present invention, the sensor 10 is provided in a form of a so-called cuff. FIG. 4 illustrates a configuration of the biological signal measuring system 1 according to this exemplary embodiment. The biological signal measuring system 1 has the configuration in which a cuff 30 is used as an example of the sensor 10 shown in FIGS. 1 and 3. The biological signal measuring apparatus 20 includes an inflation pump 24, a pressure sensor 25, and a discharge valve 26 as a specific mode for controlling the pressure of the cuff 30. The controller 21 has a blood pressure calculator 213 which noninvasively calculates the blood pressure of the subject, in addition to the blood refill time measuring section 212.

A configuration of the cuff 30 will be described in detail with reference to FIGS. 5A and 5B. FIG. 5A is an external view of the cuff 30. As illustrated, the cuff 30 is wrapped around the upper arm or the lower limb to be fixed thereto, in a similar manner as typical cuffs for non-invasive measurement. The cuff 30 has a hook-and-loop fastener 31 on the contact surface 16 that contacts the subject, and another hook-and-loop fastener 32 on a surface opposite to the contact surface 16. In one of the hook-and-loop fasteners 31, 32, fibers are raised in a hook manner, and, in the other fastener, fibers are densely raised in a loop manner. When the hook-and-loop fasteners 31, 32 are pressed against each other, the cuff can be secured to the subject. The hook-and-loop fasteners 31, 32 may be provided in another form such as a click type fastener or a shark bite fastener as far as the cuff can be secured to the subject. The cuff 30 is connected to the biological signal measuring apparatus 20 through a tube 33. In place of the use of the hook-and-loop fasteners 31, 32, an adhesive member such as an adhesive tape may be used in the place where the hook-and-loop fastener 31 is disposed, and the cuff 30 may be secured to the subject.

FIG. 5B is a front view of the contact surface 16 of the cuff 30 (the side on which the cuff 30 contacts a surface of a body of a subject). In the example, a bag 34 is placed so as to cover the light emitter 11 and the light receiver 13. The bag 34 corresponds to the light blocking member 15 in FIG. 3. That is, the bag 34 has also the function of blocking light passing between the light emitter 11 and the light receiver 13. Therefore, the bag 34 is a bag which is made of a material such as colored polyvinyl chloride or polyurethane, and into which gas (mainly air) can be flown (charged). An air inflow control is performed on the bag 34 by the biological signal measuring apparatus 20. When gas is sent into the bag 34, the bag is inflated, and compresses the living tissue of the subject.

Figure 6A:
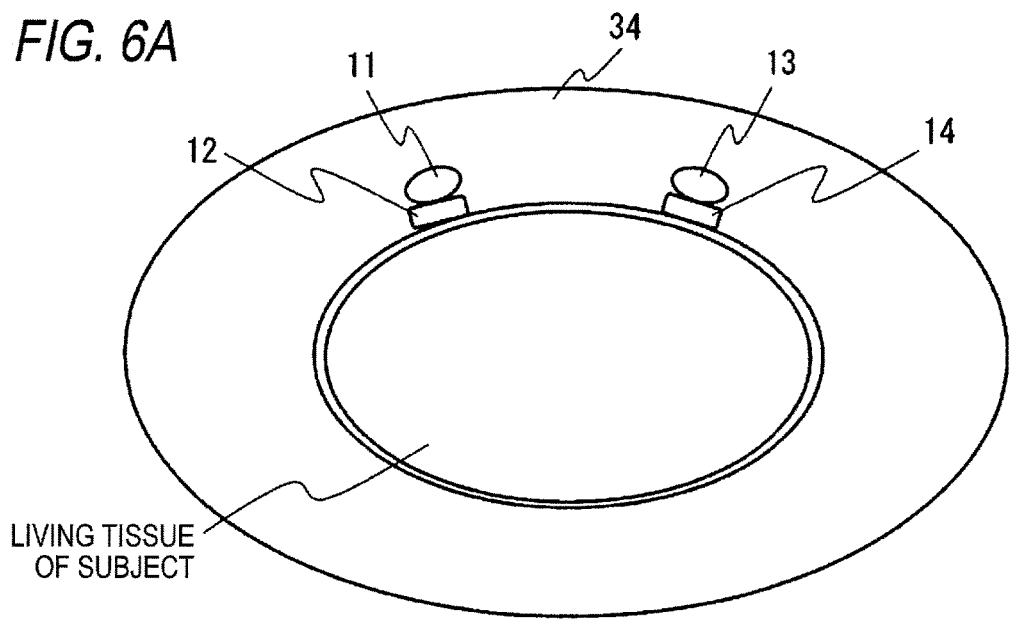
FIGS. 6A and 6B are diagrams illustrating examples of the cuff.
Figure 6B:
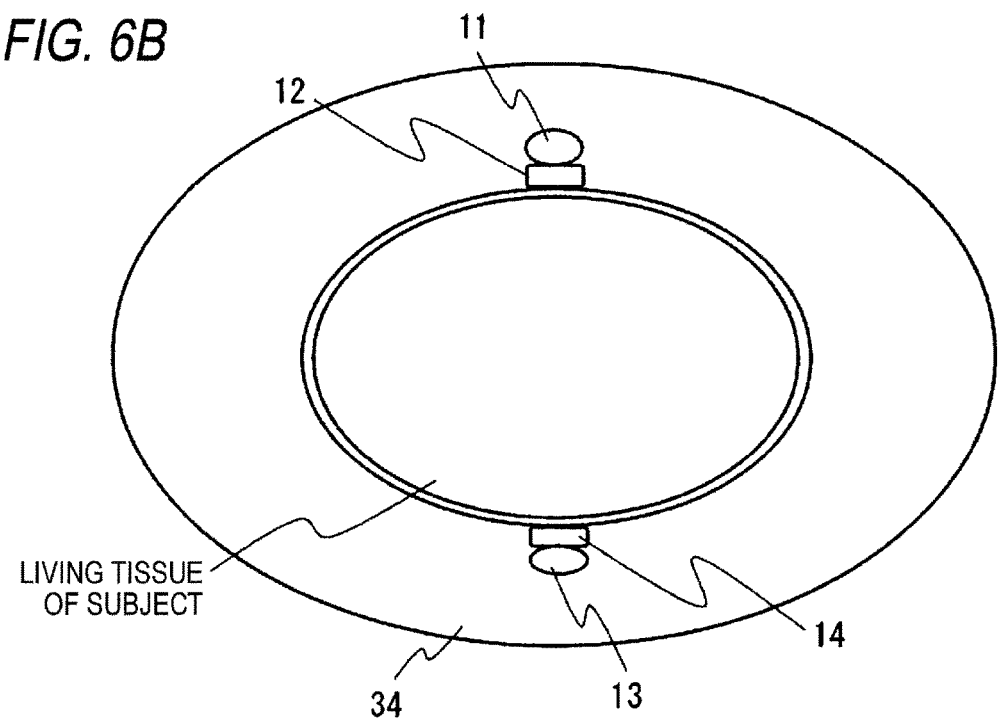

FIGS. 6A and 6B are views showing the concept of the attachment of the cuff 30. FIG. 6A is a conceptual view showing the cuff 30 of the reflection type. In the configuration, the light receiver 13 receives light (reflected light) which is emitted by the light emitter 11 and then reflected from the living tissue.

FIG. 6B shows an example of attachment of the cuff 30 in which the light emitter 11 and the light receiver 13 are substantially opposed to each other across the living tissue. In the attachment example, the light receiver 13 receives light (transmitted light) which is emitted by the light emitter 11 and then transmitted through the living tissue.

Referring again to FIG. 4, under the control of the pressure adjusting section 211, the inflation pump 24, the pressure sensor 25, and the discharge valve 26 perform the pressure rise/fall of the cuff 30 and detect the cuff pressure. For example, the inflation pump 24 is a low-flow-rate air pump such as a rolling pump having a plurality of cylinders. The pressure sensor 25 detects the air pressure (cuff pressure) in the cuff 30. An oscillation signal indicating the detected cuff pressure is processed in an A/D converter (not shown) and the like, and is then sent to the pressure adjusting section 211 and the blood pressure calculator 213. Under the control of the pressure adjusting section 211, the discharge valve 26 is driven to discharge the gas (mainly air) in the cuff 30.

The blood pressure calculator 213 calculates the blood pressure of the subject based on the displacement of the oscillation signal. The blood pressure calculator 213 is configured to performs a non-invasive blood pressure measurement by linear inflation method. The non-invasive blood pressure measurement by linear inflation method may be implemented by, for example, a system similar to that disclosed in JP2012-40088A or Nihon Kohden's website "Bedside Monitor BSM-1700 series—Life Scope PT", accessible as of Sep. 22, 2014 at www.nihonkohden.co.jp/iryo/products/monitor/01_bedside/bsm1700.html.

Following is a brief description of a linear inflation non-invasive blood pressure measurement performed by the blood pressure calculator 213. The pressure adjusting section 211 raises the cuff pressure to a first set value. The blood pressure calculator 213 identifies the systolic blood pressure and the diastolic blood pressure by using the oscillation signal which is varied in accordance with the pressure rise. In the case where both the identified systolic and diastolic blood pressures are normal values, the pressure adjusting section 211 terminates the pressure rise of the cuff 30, and immediately releases the cuff pressure. In the case where at least one of the systolic blood pressure and diastolic blood pressure which are identified by the blood pressure calculator 213 is an abnormal value, by contrast, the pressure adjusting section 211 raises the cuff pressure to a second set value, and then lowers the pressure. The blood pressure calculator 213 identifies the blood pressure based on a change of the oscillation signal during the falling. As for the details of the linear inflation method, see, e.g., FIGS. 2 and 3 of JP2012-40088A.

FIG. 7 is a conceptual view showing relationships between a rise of the cuff pressure and the oscillation signal before the cuff pressure reaches the first set value. In accordance with the pressure rise of the cuff 30, the amplitude of the oscillation signal is increased. The blood pressure calculator 213 detects a change point TL where the oscillation amplitude is rapidly increased, as the diastolic blood pressure (minimal blood pressure). Moreover, the blood pressure calculator 213 detects a change point TH where the oscillation amplitude is gradually reduced after the amplitude becomes maximum, and rapidly lowered, as the systolic blood pressure (maximal blood pressure). In the case where the diastolic blood pressure (minimal blood pressure) and the systolic blood pressure (maximal blood pressure) are normal values, deflation of the cuff is started (TX).

In parallel with the measurement of the blood pressure, the biological signal measuring apparatus 20 measures also the blood refill time. Firstly, the cuff 30 measures the amount of light received from the living tissue before the rise of the cuff pressure (corresponding to S12 of FIG. 2). Then, the cuff 30 measures the amount of light received from the living tissue during the pressure rise (corresponding to S14 of FIG. 2). The blood refill time measuring section 212 computes or calculates the time elapsed from the timing when the living tissue is released from pressure (timing when the cuff pressure is released, corresponding to TX of FIG. 7), until when the amount of received light attenuates to a predetermined ratio with respect to the increment of the amount of received light due to the pressure on the living tissue, as the blood refill time (corresponding to S16 of FIG. 2). This processing is merely an example. For example, data for the blood pressure measurement may be acquired after starting the inflation, and the blood refill time may be measured after acquiring the data for the blood pressure measurement. That is, the biological signal measuring apparatus 20 may calculate the blood pressure and the blood refill time after the inflation (i.e., after acquiring the necessary data), or may sequentially calculate the blood pressure during the inflation.

As described above, the biological signal measuring apparatus 20 is configured to calculate the blood refill time of the subject based on the amount of received light acquired by the cuff 30 (i.e., by the sensor 10), and to calculate the blood pressure of the subject based on the pressure change acquired by the cuff 30 (i.e., by the sensor 10). The biological signal measuring apparatus 20 may be configured to always calculate the blood refill time and the blood pressure, or may perform calculation (measurement of only the blood refill time, measurement of only the blood pressure, or measurement of the blood refill time and the blood pressure) in accordance with a mode setting by a user (e.g., setting by an operation of a button). With the configuration that allows the mode setting, a measurement that is required in accordance with the condition of the subject can be performed, and the measurement time can be shortened by not performing an unnecessary measurement.

It is preferable that at least one of the timing of measuring the blood pressure and the timing of measuring the blood refill time be set optionally by the user. That is, only the timing of measuring the blood pressure, only the timing of measuring the blood refill time, or both of the timing of measuring the blood pressure and the timing of measuring the blood refill time may be set. For example, the user may perform setting so that the blood pressure is measured every 30 minutes, and the blood refill time is measured every one hour. The biological signal measuring system 1 automatically controls measurements of parameters in accordance with the setting.

Advantages of the cuff 30 and biological signal measuring system 1 of the embodiment will be described. In the fingertip to which a pulse oximeter or the like is to be attached, sometimes, the blood flow is caused not to correctly reflect the operation of the central circulation, by an influence of the temperature of the nervous system. By contrast, the blood flow in a portion such as the upper arm or the lower limb is less affected by the temperature and the activity of the nervous system, as compared to the fingertip. The cuff 30 has a usual cuff shape (FIGS. 5A and 5B) for the non-invasive blood pressure measurement, and therefore can be rapidly attached to the upper arm or lower limb of the subject. When the measurement is performed on the upper arm or the lower limb, it is possible to measure the blood refill time to which the condition of the central circulation is reflected. Since the measurement place can be set in the upper arm or the lower limb, the blood refill time can be correctly measured even when the body size of the subject is small (for example, when the subject is a child).

In order to measure the blood refill time, gas (mainly air) is sent into the cuff 30, the cuff 30 compresses the living tissue, and then the pressure is released by discharging the gas. This operation is substantially the same as that of the cuff in non-invasive blood pressure measurement. Therefore, the biological signal measuring apparatus 20 can perform the non-invasive blood pressure measurement in addition to the measurement of the blood refill time. With a single application of pressure on the living tissue and a release of the pressure, the two parameters can be measured, and therefore the burden on the subject can be reduced. The single biological signal measuring apparatus 20 can measure the two parameters, and therefore cost reduction and miniaturization of the apparatus can be realized.

The biological signal measuring apparatus 20 may be configured to perform a linear inflation non-invasive blood pressure measurement as disclosed in JP2012-40088A (FIG. 7). In accordance with the setting by the user, the blood pressure and the blood refill time may be measured at the same timing. In this case, when the systolic blood pressure and the diastolic blood pressure can be correctly measured during the pressure rise to the first set value, the pressure rise is immediately ended, and the pressure fall is started. According to the configuration, the biological signal measuring apparatus 20 can measure the blood pressure in a time period which is shorter than that in the case of the usual blood pressure measuring system (the system in which the cuff pressure is firstly raised to a sufficiently high pressure, and, while then lowering the cuff pressure, the oscillation signal is acquired). The biological signal measuring apparatus 20 starts the measurement of the blood refill time at the timing when the pressure lowering is started. Since the pressure raising time can be made short, the biological signal measuring apparatus 20 can end also the measurement of the blood refill time in a short time period.

It is a matter of course that a configuration may be possible where, while measuring the blood refill time, the blood pressure is calculated by using the usual blood pressure measuring system (the system in which the cuff pressure is firstly raised to a sufficiently high pressure, and, while then lowering the cuff pressure, the oscillation signal is acquired).

By allowing the user to set the timing of measuring the blood pressure and the timing of measuring the blood refill time, the blood pressure and the blood refill time can be automatically acquired without performing starting operations on buttons and the like each time. By associating the timing of measuring the blood pressure with the timing of measuring the blood refill time (e.g., when the blood pressure is measured every 30 minutes, the blood refill time is measured every 30 minutes or every one hour), the two parameters can be simultaneously measured in a single step of performing the pressure raising and falling on the living tissue, so that the burden on the subject can be reduced.

In the above-described configuration, both of the blood pressure and the blood refill time are measured in accordance with the pressure control performed on the cuff 30. However, the invention is not limited to this. Of course, the cuff 30 and the biological signal measuring apparatus 20 may be configured as a single-function apparatus which is used only for measuring the blood refill time.

It is preferable that the energy for applying pressure on the living tissue to measure the blood refill time be minimized. Therefore, the biological signal measuring apparatus 20 detects the pulsation of the cuff pressure in the process of pressurizing, and calculates the maximal blood pressure from the pulsation in a technique similar to that disclosed in JP2012-40088A. Preferably, then, the biological signal measuring apparatus 20 may end the pressure rise at the timing when the cuff pressure becomes higher than the maximal blood pressure, immediately start the pressure fall, and begin the measurement of the blood refill time. In this case, the time period of the pressure rise and pressure required for measuring the blood refill time can be reduced to the minimum necessary level. Therefore, the blood refill time can be measured without imposing excessive pressure on a subject with low blood pressure.

Figure 8:
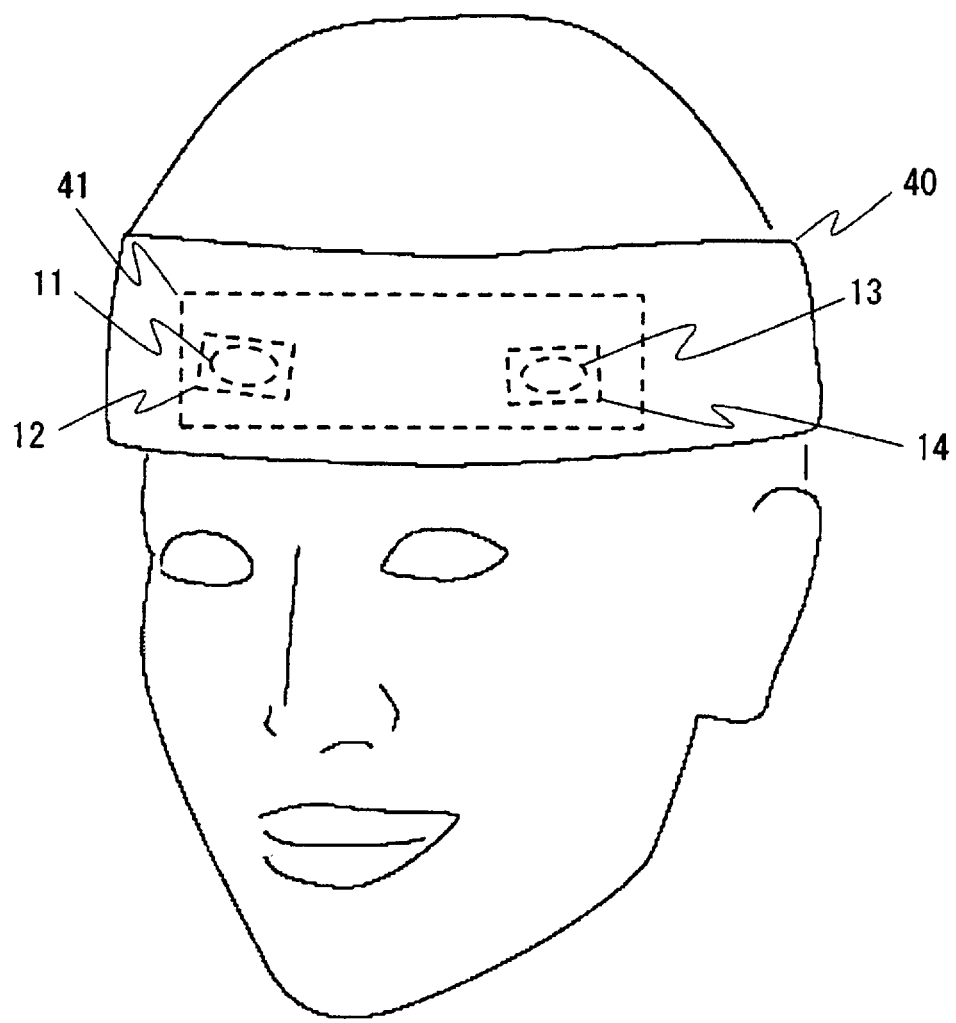
FIG. 8 is a diagram illustrating an example of an attachment of a band sensor as another example of the sensor.
Figure 9:
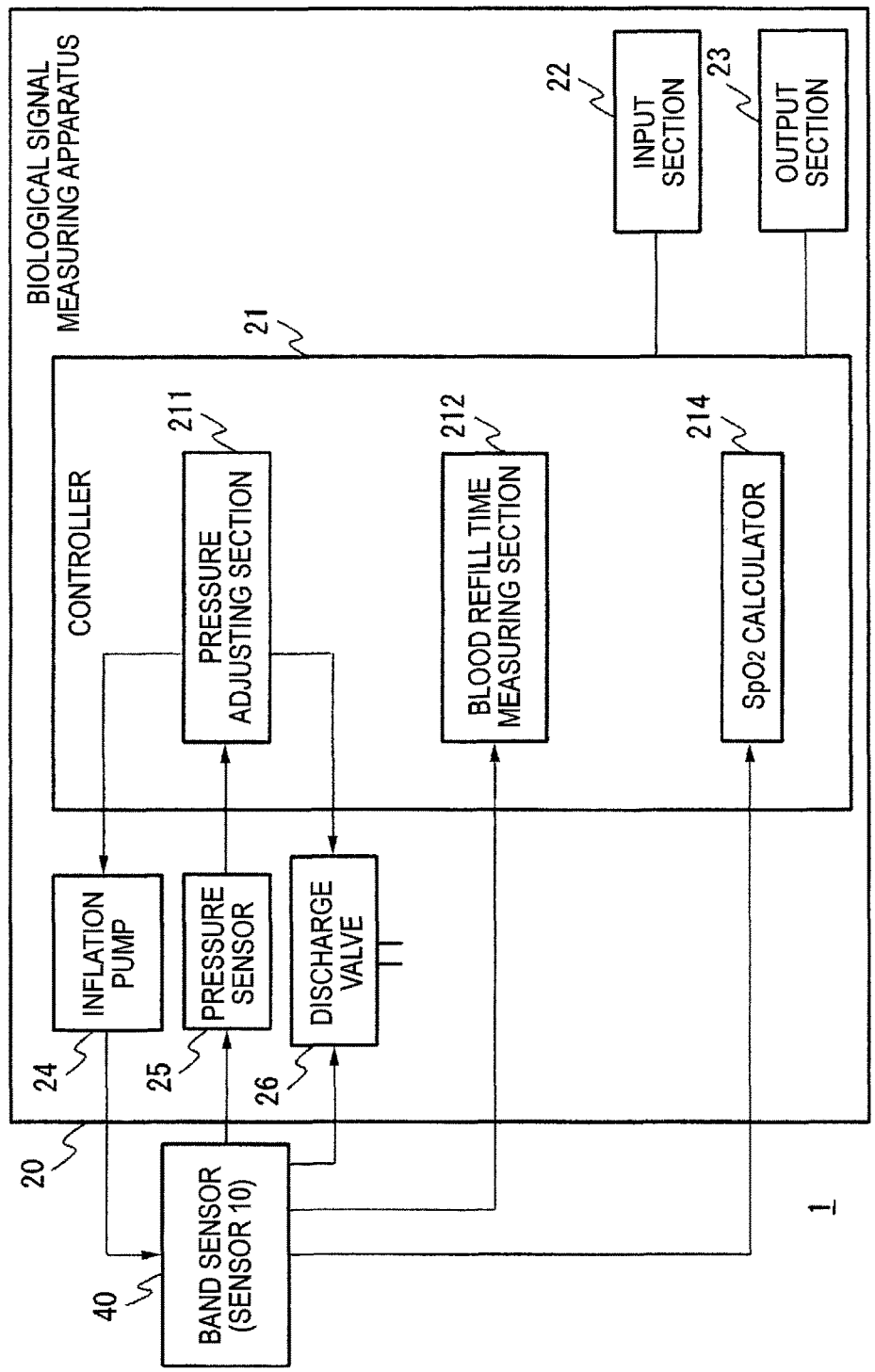
FIG. 9 is a block diagram illustrating a configuration of a biological signal measuring system according to another exemplary embodiment of the present invention.

Next, another exemplary embodiment of the present invention will be described. In this exemplary embodiment, the sensor 10 (FIG. 3) is in a form of a band (a band sensor 40), and is wrapped around a head or the like in use. FIG. 8 illustrates an example of an attachment of the band sensor 40, and FIG. 9 illustrates another example of a configuration of the biological signal measuring system 1.

As shown in FIG. 8, the band sensor 40 is configured such that the band sensor 40 is attached to a head or the like of a subject by being wrapped around the head or the like of the subject. The surface of the band sensor 40 contacting the subject corresponds to the contact surface 16 in FIG. 3.

The light emitter 11 in the embodiment emits light of a plurality of wavelengths. For example, the light emitter 11 includes a light emitting device which emits red light having a wavelength of about 660 nm, and another light emitting device which emits infrared light having a wavelength of about 940 nm. The light receiver 13 receives reflected or transmitted light of the wavelengths (660 nm and 940 nm). The light receiver 13 sends information on amounts of received light of the respective wavelengths to the biological signal measuring apparatus 20.

The band sensor 40 has inside a bag 41. When gas is sent into the bag 41, the bag is inflated, and, in the inflated condition, applies pressure on the living tissue of the subject. The air is sent into the bag 41 through a tube which is not shown, from the biological signal measuring apparatus 20. The band sensor 40 may be configured by, for example, attaching the bag 41, the light emitter 11, the light receiver 13, and the like to a member such as a band. The member functions as the light blocking member 15 in FIG. 3. The user may extend or contract the member in accordance with the attachment place of the subject.

The band sensor 40 may operate as an SpO2 sensor and also as a sensor for measuring the blood refill time. The user operates the input section 22 to designate the measurement mode (an SpO2 measurement mode, a blood refill time measurement mode, or a mode of measurement of the both parameters). When the SpO2 measurement mode is selected, the light receiver 13 detects the amounts of received light of the two wavelengths, and a pulse wave, and sends the result of the detection to the biological signal measuring apparatus 20. When the blood refill time measurement mode is selected, the band sensor 40 detects the amounts of received light before and after the application of pressure in a manner similar to the example of the cuff 30, and sends the result of the detection to the biological signal measuring apparatus 20.

Next, the biological signal measuring apparatus 20 which is to be connected to the band sensor 40 will be described with reference to FIG. 9. As compared to the configuration of FIG. 4, the biological signal measuring apparatus 20 has an SpO2 calculator 214 in place of the blood pressure calculator 213.

The SpO2 calculator 214 measures the arterial oxygen saturation (Spo2) based on the pule wave and amounts of received light of the wavelengths (the red light and the infrared light) which are detected by the band sensor 40. A calculation of the arterial oxygen saturation by the SpO2 calculator 214 is the same as the calculation using a pulse oximeter (see, e.g., JP6-30915A).

The blood refill time measuring section 212 performs the process shown in FIG. 2 to measure the blood refill time.

Although, in the above, the configuration where the light emitter 11 emits light of two wavelengths has been described, the invention is not limited to this. A configuration where light of three or more wavelengths is emitted may be employed.

Advantages of the band sensor 40 and biological signal measuring apparatus 20 of the embodiment will be described. Since the band sensor 40 has the configuration where an expandable band is used, the sensor can be attached to various locations on a subject. Therefore, like the example of the cuff, it is useful also in the case where the subject is a child or the like, and can measure the blood refill time to which the condition of the central circulation is reflected.

In the above-described configuration, the light emitter 11 emits light of two or more wavelengths, and the light receiver 13 receives light. The configuration is identical with that of a usual pulse oximeter, and therefore the blood refill time and the arterial oxygen saturation can be measured by using one identical apparatus.

Next, a modified example of the band sensor 40 will be described with reference to FIG. 10. In this example, the band sensor 40 is provided as two parts (a thin-film sheet 42 and a holding band 43). The thin-film sheet 42 is configured to contact the surface of the living tissue of the subject, and forms a sheet structure as shown in FIG. 3. The material of the thin-film sheet 42 has a light blocking property. That is, the thin-film sheet 42 functions as the light blocking member 15 that blocks the direct light transmission between the light emitter 11 and the light receiver 13. The holding band 43 has the bag 41, and holds the thin-film sheet 42 and the bag 41 onto the subject. The holding band 43 is provided in a form of a band like the example of FIG. 8. The thin-film sheet 42 and the holding band 43 are connected to the biological signal measuring apparatus 20 through a tube and wiring which are not shown.

When gas (mainly air) is sent into the bag 41, pressure is applied on the living tissue at a location where the thin-film sheet 42 is held. The methods of measuring the blood refill time and the SpO2 may be the same as the methods described above.

Also in the configuration (FIG. 10), the blood refill time of the subject who is a child or the like can be correctly measured, and a correct measurement value of the blood refill time to which the condition of the central circulation is reflected can be obtained.

Figure 10:
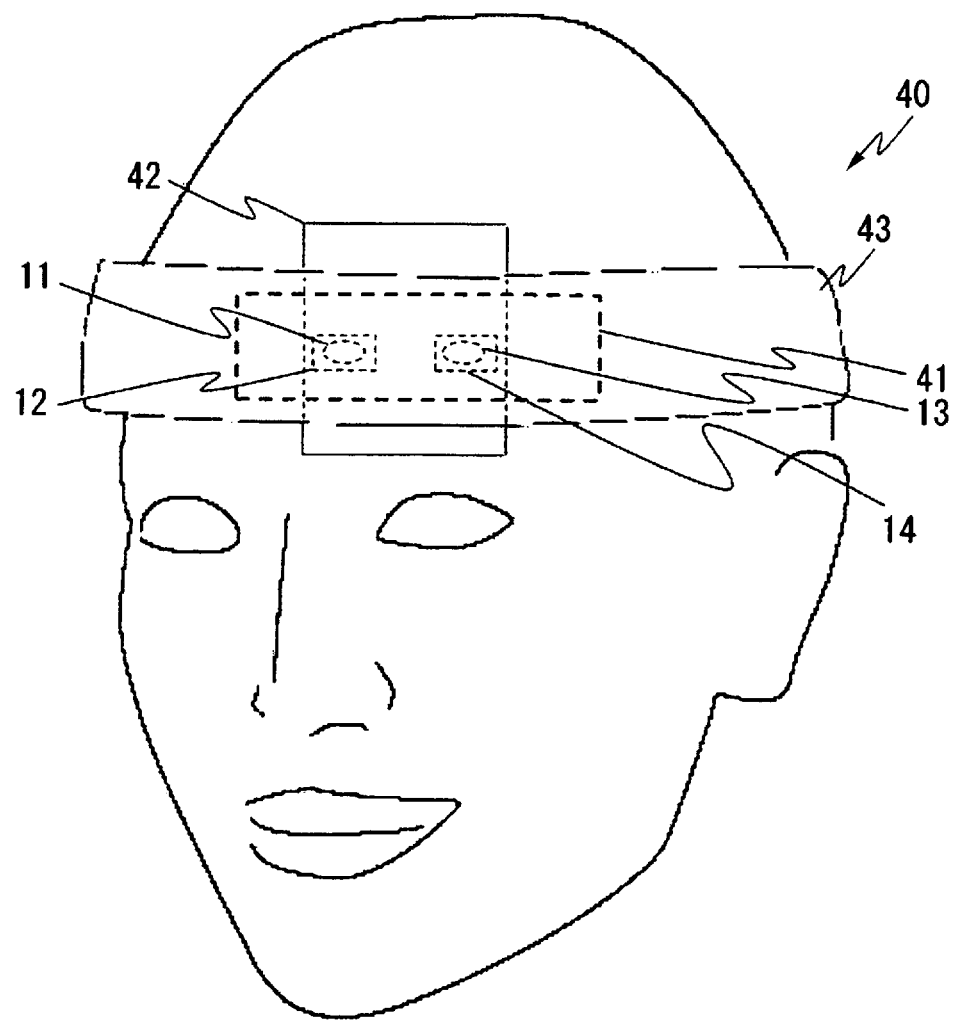
FIG. 10 is a diagram illustrating an example of an attachment of another type of band sensor.

While the configuration of FIG. 10 has been described with the thin-film sheet 42 attached to the forehead and the holding band 43 wrapped around the head, the present invention is not limited to this. The holding band 43 is merely an example of a holding member, which may not be in a form of a band. The thin-film sheet 42 may be configured such that it is attached to a non-flat portion of a body of a subject, like a finger or the like. For example, when the thin-film sheet 42 is wrapped around the finger, a holding member having an air bag may be attached on the thin-film sheet 42 so that pressure is applied to the living tissue by inflating the air bag.

According to another exemplary embodiment of the present invention, the contact surface 16 of the sensor 10 may have adhesiveness, so that the sensor 10 is attached to a subject by the contact surface 16 adhered to the subject.

Figure 11A:
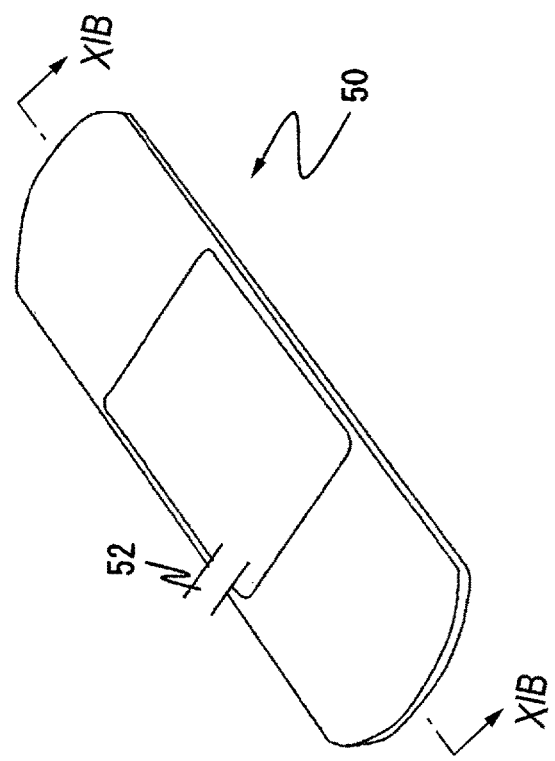
FIGS. 11A and 11B are external views of a patch sensor as another example of the sensor.
Figure 11B:
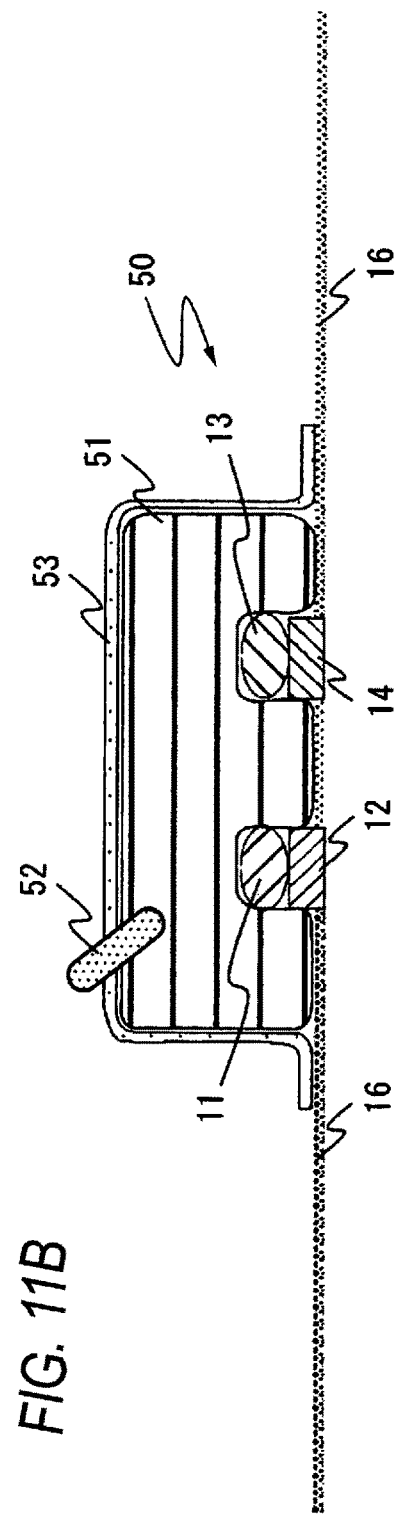

FIGS. 11A and 11B are views of a patch sensor 50 as another example of the sensor 10 shown in FIG. 3. FIG. 11A is an external view of the patch sensor 50, and FIG. 11B is a sectional view of the patch sensor 50 taken along the line A-A in FIG. 11A. The configuration of the patch sensor 50 will be described with reference to both FIGS. 11A and 11B. The configuration of the biological signal measuring apparatus 20 is substantially identical with the configurations shown in FIGS. 4 and 9, and therefore its illustration and detailed description are omitted.

The contact surface 16 of the patch sensor 50 is provided by an adhesive material which can be adhered to the subject. Specifically, the contact surface 16 may be formed by a adhesive agent which is known as a medical adhesive agent. More specifically, an acrylic-based adhesive agent, a rubber-based adhesive agent, a silicone-based adhesive agent, a vinyl ether-based adhesive agent, and the like may be used as it is or mixed with each other.

Similarly with the case of FIG. 3, the light emitter 11 emits light of a predetermined wavelength to the living tissue. The light emitted by the light emitter 11 passes through the first light transmitting member 12 and enters the living tissue. The light receiver 13 receives light (reflected light or transmitted light) from the living tissue through the second light transmitting member 14.

The biological signal measuring apparatus 20 causes gas (mainly air) to be flown into a bag 51 through a tube 52, thereby performing pressure rise and fall on the living tissue. The bag 51 functions as the light blocking member 15 in FIG. 3, and further applies and releases pressure on the living tissue. As illustrated, the bag 51 may be placed so as to be interposed between the contact surface 16 and an elastic film 53. Preferably, the elastic film 53 is made of a material having a greater elastic modulus than that of the bag 51. With the elastic film 53 having greater elastic modulus than the bag 51, a force due to the inflation of the bag 51 is efficiently applied toward the living tissue. This enables efficient application of pressure on the living tissue. The method of measuring the blood refill time is the same as the previously described examples.

Advantages of the patch sensor 50 and biological signal measuring system 1 of the embodiment will be described. The patch sensor 50 can be easily pasted to the subject by using a usual adhesive member (acrylic-based adhesive agent or the like). Moreover, the patch sensor 50 can be attached to various locations on the subject. Therefore, the blood refill time can be measured irrespective of situations such as injury or sickness, clothing, or the like of the subject. Like to the example of the cuff, it is useful also in a case where the subject is a child or the like, and can measure the blood refill time to which the condition of the central circulation is reflected.

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

For example, the cuff 30 of FIG. 5 may emit light of a plurality of wavelengths. The cuff 30 may be configured so as to emit light having wavelengths of about 660 nm, 940 nm, and 1,300 nm. The light of 1,300 nm is more largely absorbed by water than hemoglobin. When the cuff 30 is wrapped around the arm, and the received amount of the light of 1,300 nm is measured, therefore, it is possible to detect also the possibility of edema or the like.

What is claimed is:

1. A sensor configured to measure a blood refill time of a living tissue of a subject, the sensor comprising:
   a pressure applying portion configured to apply pressure on the living tissue of the subject;
   a light emitter configured to emit light toward the living tissue of the subject;

a light receiver configured to receive reflected light or transmitted light from the living tissue of the subject;

a first light transmitting member being a single-piece member made of a light transmitting material, the first light transmitting member having one end configured as a contact surface contacting the light emitter and another end forming a contact surface to contact the subject;

a second light transmitting member being a single-piece member made of a light transmitting material, the second light transmitting member having one end configured as a contact surface contacting the light receiver and another end forming the contact surface to contact the subject; and a light blocking member configured to block light between the light emitter and the light receiver.

2. The sensor according to claim 1, wherein the pressure applying portion comprises a bag configured to apply pressure on the living tissue of the subject when the bag is inflated.

3. The sensor according to claim 2, wherein the sensor is configured as a cuff that is wrapped around the subject to be held onto the subject.

4. The sensor according to claim 1, wherein the pressure applying portion is configured such that a time period from a start of a reduction of the pressure to an end of an application of the pressure is shorter than two seconds.

5. The sensor according to claim 1, wherein the contact surface to contact the subject comprises an adhesive material.

6. The sensor according to claim 5, wherein the pressure applying portion comprises a bag configured to apply pressure on the living tissue of the subject,
wherein the sensor further comprises an elastic film provided on a surface opposite to the contact surface to cover the bag, and
wherein an elastic modulus of the elastic film is greater than an elastic modulus of the bag.

7. The sensor according to claim 1, wherein the light emitter is configured to emit light of two or more wavelengths.

8. The sensor according to claim 1, further comprising a holding member on which the pressure applying portion is provided,
wherein the light blocking member comprises a thin-film sheet on which the light emitter and the light receiver are provided;
wherein the holding member is configured to hold the thin-film sheet and the pressure applying portion onto the subject.

9. A sheet structure comprising:
a light emitter configured to emit light toward a living tissue of a subject;
a light receiver configured to receive reflected light or transmitted light from the living tissue of the subject;
a first light transmitting member being a single-piece member made of a light transmitting material, the first light transmitting member having one end configured as a contact surface contacting the light emitter and another end forming a contact surface to contact the subject;
a second light transmitting member being a single-piece member made of a light transmitting material, the second light transmitting member having one end configured as a contact surface contacting the light receiver and another end forming the contact surface to contact the subject; and a thin-film sheet configured to block light between the light emitter and the light receiver, the light emitter and the light receiver being provided on the thin-film sheet.

10. A biological signal measuring system comprising:
a sensor; and
a biological signal measuring apparatus configured to calculate a blood refill time of a subject,
wherein the sensor comprises:
a pressure applying portion configured to apply pressure on a living tissue of the subject;
a light emitter configured to emit light toward the living tissue of the subject;
a light receiver configured to receive reflected light or transmitted light from the living tissue of the subject;
a first light transmitting member made of a light transmitting material, the first light transmitting member having one end configured as a contact surface contacting the light emitter and another end forming a contact surface to contact the subject;
a second light transmitting member made of a light transmitting material, the second light transmitting member having one end configured as a contact surface contacting the light receiver and another end forming the contact surface to contact the subject; and
a light blocking member configured to block light between the light emitter and the light receiver,
wherein the biological signal measuring apparatus is configured to calculate the blood refill time based on an amount of light received by the sensor.

11. A biological signal measuring system comprising:
a sensor configured as a cuff that is wrapped around a subject to be held onto the subject and configured to acquire a pressure change inside the cuff; and
a biological signal measuring apparatus configured to calculate a blood refill time of the subject and a blood pressure of the subject,
wherein the sensor comprises:
a pressure applying portion comprising a bag configured to apply pressure on a living tissue of the subject when the bag is inflated;
a light emitter configured to emit light toward the living tissue of the subject;
a light receiver configured to receive reflected light or transmitted light from the living tissue of the subject;
a first light transmitting member made of a light transmitting material, the first light transmitting member having one end configured as a contact surface contacting the light emitter and another end forming a contact surface to contact the subject;
a second light transmitting member made of a light transmitting material, the second light transmitting member having one end configured as a contact surface contacting the light receiver and another end forming the contact surface to contact the subject; and
a light blocking member configured to block light between the light emitter and the light receiver,
wherein biological signal measuring apparatus is configured to calculate the blood refill time of the subject based on an amount of light received by the sensor, and to calculate the blood pressure of the subject based on the pressure change inside the cuff acquired by the sensor.

12. The biological signal measuring system according to claim 11, wherein the biological signal measuring apparatus comprises an input section allowing a user to select one of a first mode, a second mode and a third mode, and is configured to calculate the blood refill time of the subject when the first mode is selected, to calculate the blood pressure of the subject when the second mode is selected, and to calculate the both of the blood refill time of the subject and the blood pressure of the subject when the third mode is selected.

13. The biological signal measuring system according to claim 11, wherein the biological signal measuring apparatus is configured to calculate the blood refill time of the subject at a timing that has been set.

14. The biological signal measuring system according to claim 11, wherein the biological signal measuring apparatus is configured to calculate the blood pressure of the subject at a timing that has been set.

15. The biological signal measuring system according to claim 11, wherein the biological signal measuring apparatus is configured to start acquiring data to be used for a calculation of the blood pressure of the subject after the sensor starts an application of pressure on the living tissue of the subject, to end the application of pressure on the living tissue of the subject after acquiring the data to be used for the calculation of the blood pressure is ended, and to start measuring the blood refill time of the subject by using a change of amount of received light after the application of pressure is ended.

16. A sensor configured to measure a blood refill time of a living tissue of a subject, the sensor comprising:
    a pressure applying portion having a bag configured to apply pressure on the living tissue of the subject;
    a light emitter configured to emit light toward the living tissue of the subject;
    a light receiver configured to receive reflected light or transmitted light from the living tissue of the subject;
    a light blocking member arranged between the light emitter and the light receiver;
    a light transmitting material forming a contact surface to contact the subject; and
    an elastic film provided on a surface opposite to the contact surface to cover the bag,
    wherein the light emitter and the light receiver are attached to the living tissue of the subject via the light transmitting material,
    wherein the light blocking member has a second light transmission rate that is lower than a first light transmission rate of the light transmitting material, and
    wherein an elastic modulus of the elastic film is greater than an elastic modulus of the bag.

* * * * *